United States Patent
Ohishi

(10) Patent No.: US 9,330,481 B2
(45) Date of Patent: May 3, 2016

(54) MEDICAL IMAGE PROCESSING APPARATUS AND MEDICAL IMAGE PROCESSING METHOD

(71) Applicants: KABUSHIKI KAISHA TOSHIBA, Tokyo (JP); TOSHIBA MEDICAL SYSTEMS CORPORATION, Otawara-shi, Tochigi (JP)

(72) Inventor: Satoru Ohishi, Otawara (JP)

(73) Assignees: KABUSHIKI KAISHA TOSHIBA, Tokyo (JP); TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 0 days.

(21) Appl. No.: 14/268,513

(22) Filed: May 2, 2014

(65) Prior Publication Data

US 2014/0241607 A1 Aug. 28, 2014

Related U.S. Application Data

(62) Division of application No. 12/708,667, filed on Feb. 19, 2010, now abandoned.

(30) Foreign Application Priority Data

Feb. 23, 2009 (JP) .................................. 2009-039849

(51) Int. Cl.
*G06T 11/00* (2006.01)
*A61B 6/00* (2006.01)
(Continued)

(52) U.S. Cl.
CPC ............ *G06T 11/008* (2013.01); *A61B 6/4441* (2013.01); *A61B 6/4464* (2013.01);
(Continued)

(58) Field of Classification Search
None
See application file for complete search history.

(56) References Cited

U.S. PATENT DOCUMENTS

| | | | | |
|---|---|---|---|---|
| 5,712,895 A | * | 1/1998 | Negrelli | A61B 6/583 378/207 |
| 5,782,762 A | * | 7/1998 | Vining | G06T 7/0012 128/920 |

(Continued)

FOREIGN PATENT DOCUMENTS

| | | |
|---|---|---|
| CN | 1781450 A | 6/2006 |
| CN | 101028194 A | 9/2007 |

(Continued)

OTHER PUBLICATIONS

Chinese Office Action with its English translation for Chinese Patent Application No. 201110443113.5 mailed on Jan. 10, 2014.

(Continued)

*Primary Examiner* — Tsung-Yin Tsai
(74) *Attorney, Agent, or Firm* — Yoshida & Associates, LLC

(57) ABSTRACT

A medical image processing apparatus is configured as follows. Namely the apparatus is provided with a first image generation unit which executes reconfiguration processing based on X-ray transmission data to generate a contrast blood vessel figure three-dimensional image data including a figure of a blood vessel in a subject having a contrast media injected thereto, a second image generation unit which executes reconfiguration processing based on the X-ray transmission data to generate a human anatomy figure three-dimensional image data including a figure of a human anatomy in the subject having no contrast media injected thereto, a black-and-white reverse processing unit which executes black-and-white reverse processing with respect to the contrast blood vessel figure three-dimensional image data to generate black-and-white reversed three-dimensional image data, and a combination processing unit which combines the human anatomy figure three-dimensional image data with the black-and-white reversed three-dimensional image data to generate combined image data.

6 Claims, 8 Drawing Sheets

(51) Int. Cl.
*G06T 7/00* (2006.01)
*A61B 6/06* (2006.01)

(52) U.S. Cl.
CPC ............... *A61B 6/466* (2013.01); *A61B 6/481* (2013.01); *A61B 6/501* (2013.01); *A61B 6/504* (2013.01); *A61B 6/507* (2013.01); *A61B 6/5235* (2013.01); *A61B 6/5247* (2013.01); *G06T 7/0016* (2013.01); *A61B 6/06* (2013.01); *G06T 2207/10081* (2013.01); *G06T 2207/20224* (2013.01); *G06T 2207/30101* (2013.01)

(56) References Cited

U.S. PATENT DOCUMENTS

| | | | | |
|---|---|---|---|---|
| 5,802,133 | A * | 9/1998 | Kawai | A61B 6/032 378/4 |
| 5,839,440 | A * | 11/1998 | Liou | G06T 7/0028 345/419 |
| 5,852,646 | A * | 12/1998 | Klotz | G06T 11/008 378/8 |
| 6,370,417 | B1 * | 4/2002 | Horbaschek | A61B 6/12 378/20 |
| 6,493,569 | B2 * | 12/2002 | Foo | G01R 33/5601 324/307 |
| 7,123,760 | B2 * | 10/2006 | Mullick | G06T 5/50 378/21 |
| 7,432,924 | B2 * | 10/2008 | Ohishi | A61B 6/481 345/419 |
| 2002/0154801 | A1 * | 10/2002 | Ohishi | G06T 3/0087 382/132 |
| 2003/0031299 | A1 * | 2/2003 | Ohishi | A61B 6/481 378/162 |
| 2005/0046644 | A1 | 3/2005 | Ohishi | |
| 2006/0132483 | A1 | 6/2006 | Ohishi | |
| 2008/0009716 | A1 * | 1/2008 | Ohishi | G06T 7/0042 600/425 |
| 2008/0137935 | A1 | 6/2008 | Spahn | |
| 2008/0304615 | A1 | 12/2008 | Mielekamp | |
| 2010/0128942 | A1 * | 5/2010 | Licato | G06T 7/0014 382/128 |
| 2010/0172567 | A1 * | 7/2010 | Prokoski | A61B 5/0064 382/132 |
| 2011/0299749 | A1 * | 12/2011 | Rauch | G06T 7/2053 382/130 |
| 2013/0188771 | A1 * | 7/2013 | Kyriakou | A61B 6/032 378/19 |

FOREIGN PATENT DOCUMENTS

| | | |
|---|---|---|
| JP | 2531243 B2 | 12/1989 |
| JP | 03-251232 A | 11/1991 |
| JP | 09-149902 A | 6/1997 |
| JP | 09-214835 A | 8/1997 |
| JP | 2000-217035 A | 8/2000 |
| JP | 2005-80285 A | 3/2005 |
| JP | 2005-080285 A | 3/2005 |
| JP | 2006-34355 A | 2/2006 |
| JP | 2006-034355 A | 2/2006 |
| JP | 2006-325629 A | 12/2006 |
| JP | 2006-341085 A | 12/2006 |
| JP | 2007-054623 A | 3/2007 |
| JP | 2007-130244 A | 5/2007 |
| JP | 2007-135699 A | 6/2007 |
| JP | 2008-509773 A | 4/2008 |
| JP | 2008-148932 A | 7/2008 |
| WO | 2006/057304 A1 | 6/2006 |
| WO | 2008/013255 A1 | 1/2008 |

OTHER PUBLICATIONS

Chinese Office Action with its English translation for Chinese Patent Application No. 201010118910.1 mailed on Mar. 28, 2013.
Chinese Office Action with its English translation for Chinese Patent Application No. 201010118910.1 mailed on Jun. 27, 2011.
Japanese Office Action with its English translation for Japanese Patent Application No. 2009-039849 mailed on Apr. 16, 2013.

* cited by examiner

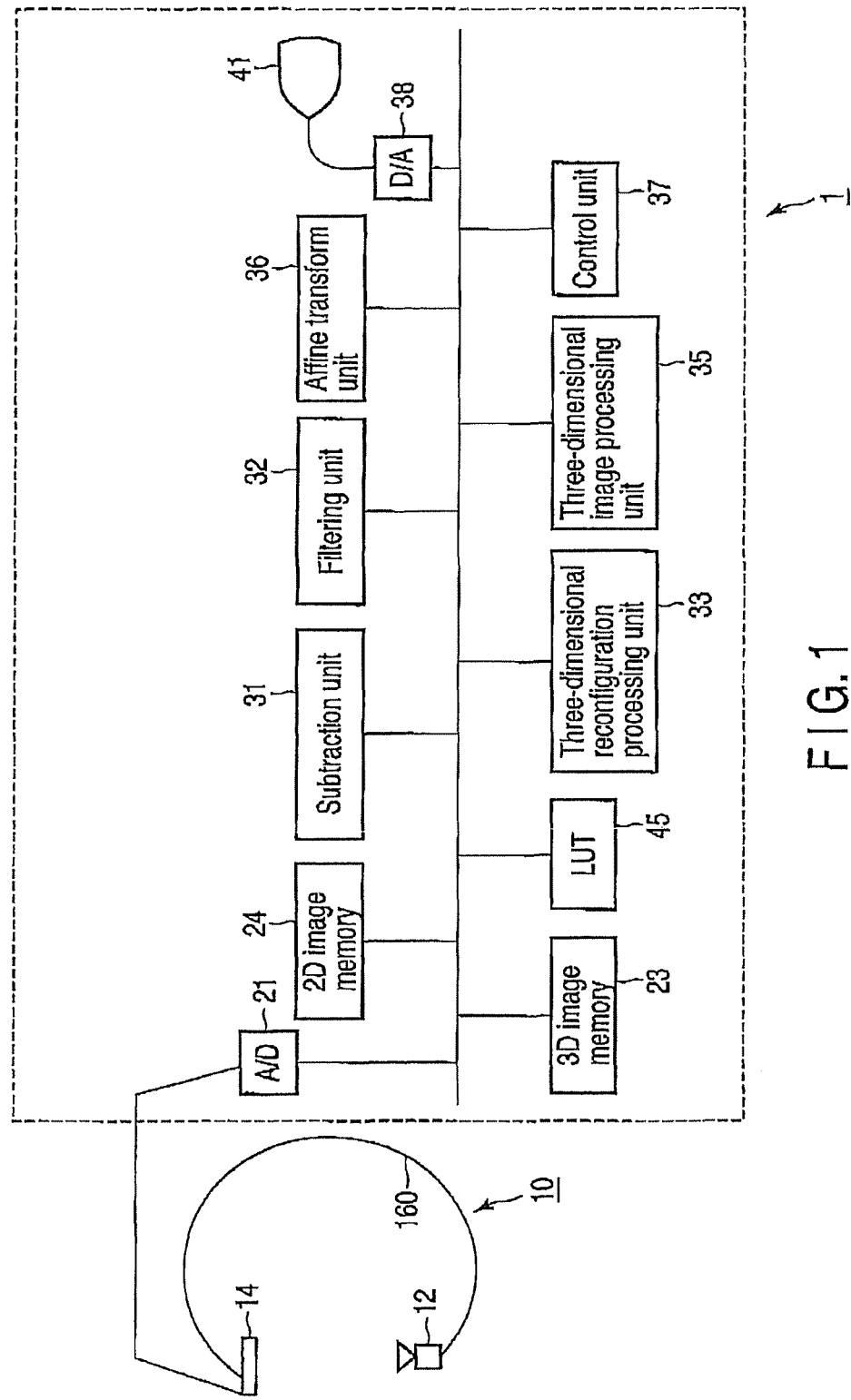
F I G. 1

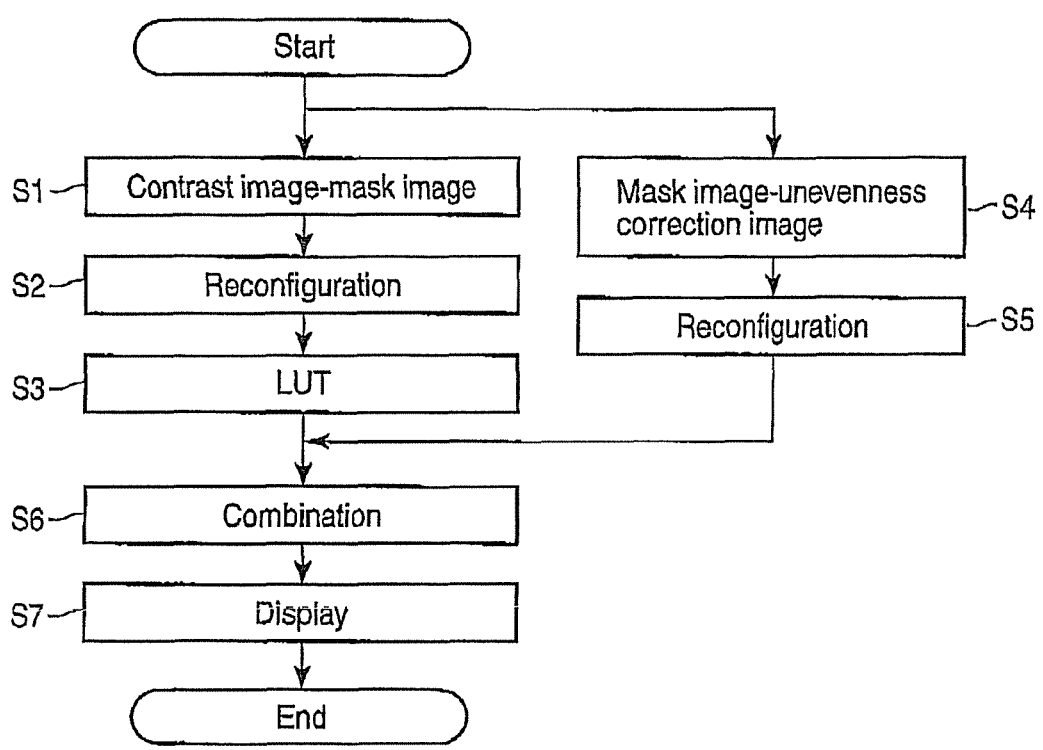
F I G. 2

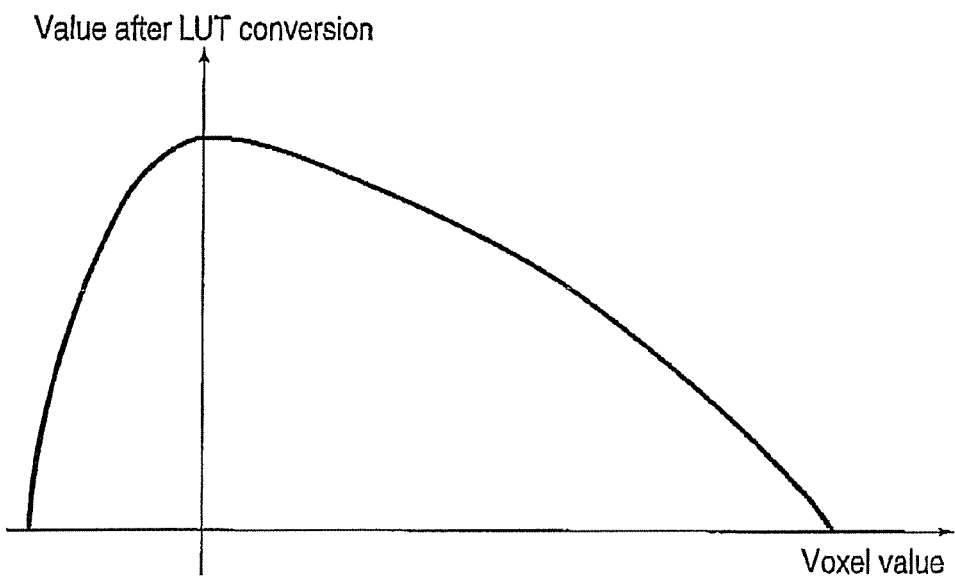
F I G. 3 A
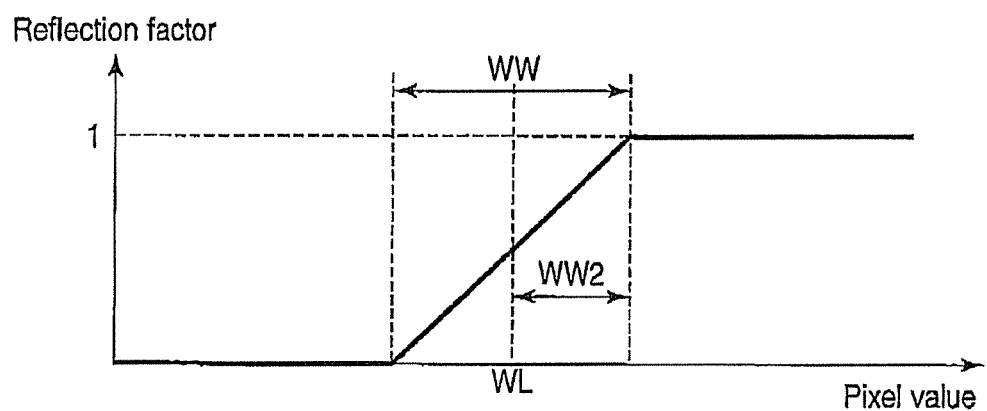
F I G. 3 B

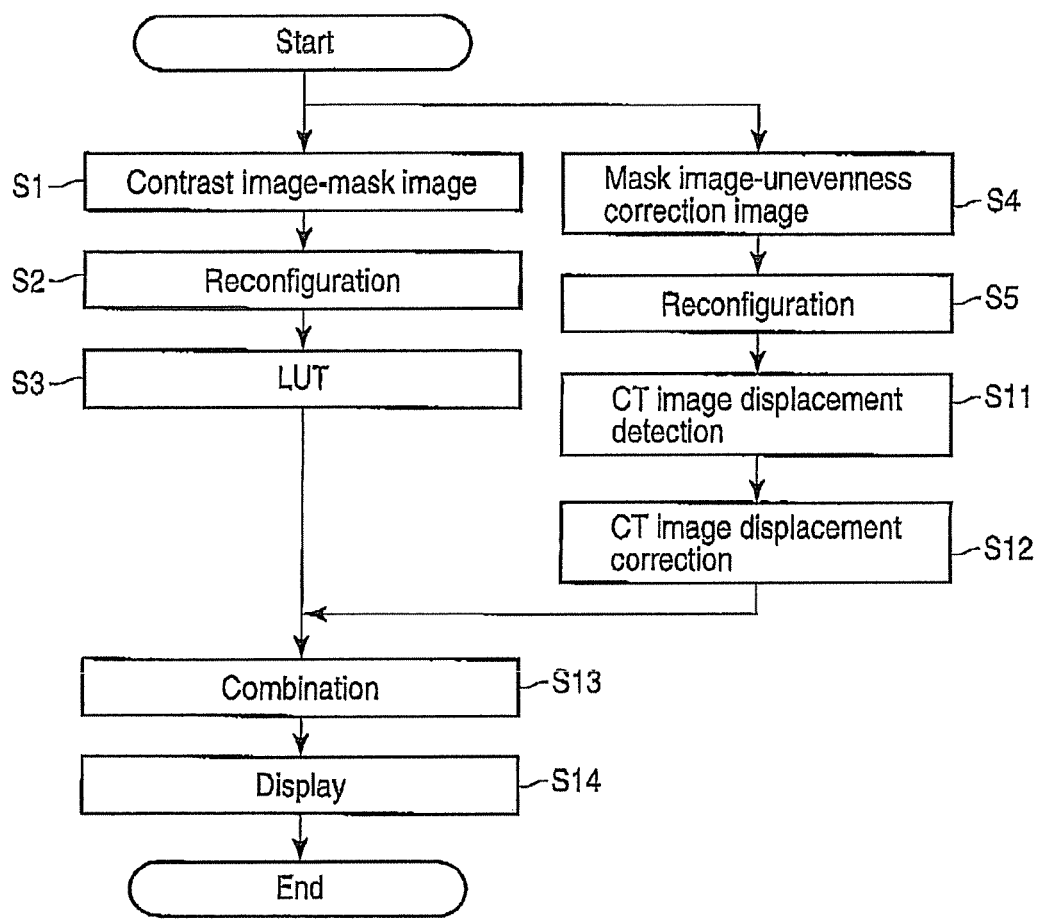
F I G. 4

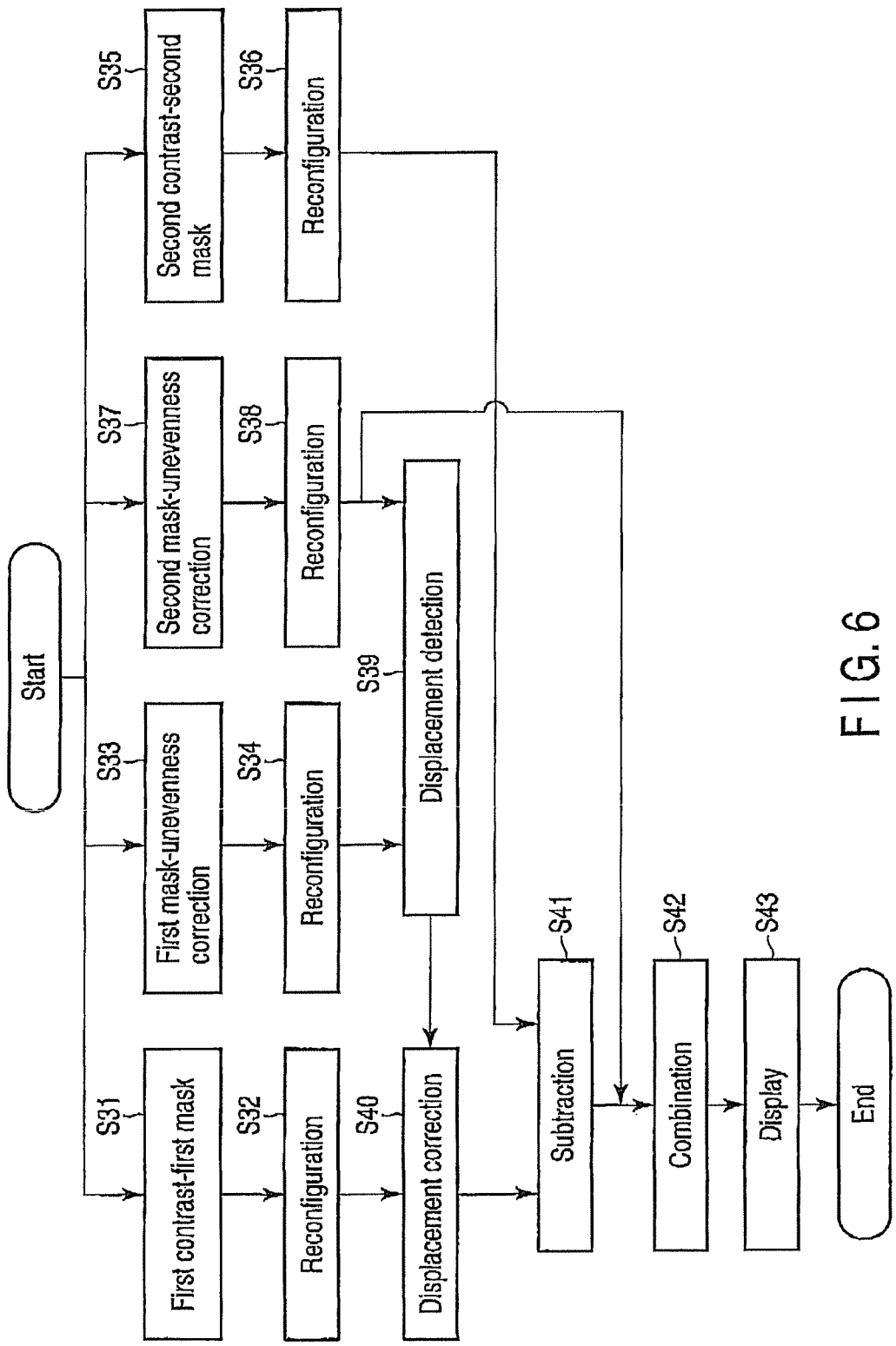
F I G. 6

MEDICAL IMAGE PROCESSING APPARATUS AND MEDICAL IMAGE PROCESSING METHOD

CROSS-REFERENCE TO RELATED APPLICATIONS

This is a divisional of U.S. application Ser. No. 12/708,667 filed on Feb. 19, 2010 under 37 CFR 1.53(b), which is based upon and claims the benefit of priority from prior Japanese Patent Application No. 2009-039849, filed Feb. 23, 2009, the entire contents of which are incorporated herein by reference.

BACKGROUND OF THE INVENTION

1. Field of the Invention

The present invention relates to a medical image processing apparatus and a medical image processing method.

2. Description of the Related Art

In diagnoses of stroke, a brain perfusion technology is useful. According to this technology, a brain perfusion image as an image showing a recirculation state of blood is created from a tomographic view of a brain taken after injection of a contrast media, and this image is often used for diagnoses for stroke.

In recent years, to three-dimensionally grasp a positional relationship between a blood vessel and a lesion, digital subtraction angiography (DSA) is used. In this DSA, 3D-DSA adopting a three-dimensional photographing method based on photography in many directions rather than photography in one direction or rotational DSA photography is often utilized.

As a technology concerning the 3D-DSA, for example, JP-A 2005-80285 (KOKAI) discloses the following technology. That is, in JP-A 2005-80285 (KOKAI), a necessary part in a subject is photographed without including an image of a contrast media, and image data of a mask image as an X-ray image is collected. Then, the necessary part including an image of the contrast media is photographed, and image data of a contrast image as an X-ray image is collected. Further, the mask image and the contrast image having the same projection angle are subjected to subtraction. Contrast blood vessel figure three-dimensional image data is reconfigured from this subtraction image. Furthermore, the mask image and air-calibration image data are subjected to subtraction, and human anatomy figure three-dimensional image data is reconfigured from this subtraction image. Moreover, the contrast blood vessel figure three-dimensional image data is combined with the human anatomy figure three-dimensional image data to be displayed. Based on this display, it is possible to clearly grasp not only detailed information of the blood vessel but also a relationship between the blood vessel and the human anatomy, especially between the blood vessel and bones.

With advancement of interventional radiology (IVR) technology in recent years, an X-ray intervention is often used for treatments of blood vessel disorders. In the X-ray intervention, a material such as plaque may scatter peripherad due to a treatment for widening stenosis by using a balloon and hence a peripheral blood vessel may possibly clogs. In such a case, thrombolysis must be rapidly performed. At this time, a time until a blood clot dissolves and a blood stream in a corresponding peripheral blood vessel is restored is an index representing a degree of dysfunction that remains in the brain.

At the present day, there is no clinically established brain perfusion technology that can be used in the X-ray intervention. Therefore, at the end of the X-ray intervention, whether an artery having a given thickness is clogged is just confirmed.

It is to be noted that CT examination conducted after the end of the X-ray intervention may enable discovering an abnormality, e.g., clog in a very thin artery or a capillary blood vessel by a blood clot in some cases. However, it is often the case that the CT examination is generally carried out at least 2 or 3 hours after the end of the X-ray intervention or on the following day of the X-ray intervention. Therefore, even if a thrombolytic therapy is rapidly effected after this discovery, a certain level of disorder may remain in the brain function in some cases.

BRIEF SUMMARY OF THE INVENTION

According to a first aspect of the invention, there is provided a medical image processing apparatus which processes X-ray transmission data collected by using rotatably supported X-ray photographing unit, comprising:

a first image generation unit which executes reconfiguration processing based on the X-ray transmission data to generate a contrast blood vessel figure three-dimensional image data including a figure of a blood vessel in a subject having a contrast media injected thereto;

a second image generation unit which executes reconfiguration processing based on the X-ray transmission data to generate a human anatomy figure three-dimensional image data including a figure of a human anatomy in the subject having no contrast media injected thereto;

a black-and-white reverse processing unit which executes black-and-white reverse processing with respect to the contrast blood vessel figure three-dimensional image data to generate black-and-white reversed three-dimensional image data; and a combination processing unit which combines the human anatomy figure three-dimensional image data with the black-and-white reversed three-dimensional image data to generate combined image data.

According to a second aspect of the invention, there is provided a medical image processing apparatus which processes X-ray transmission data collected by using rotatably supported X-ray photographing unit, comprising:

a first image generation unit which executes reconfiguration processing based on the X-ray transmission data to generate a contrast blood vessel figure three-dimensional image data including a figure of a blood vessel in a subject having a contrast media injected thereto;

a second image generation unit which executes reconfiguration processing based on the X-ray transmission data to generate a human anatomy figure three-dimensional image data including a figure of a human anatomy in the subject having no contrast media injected thereto;

an image processing unit which generates low-blood current region figure image data indicating a low-blood current region based on the contrast blood vessel figure three-dimensional image data; and a combination processing unit which combines the human anatomy figure three-dimensional image data with the low-blood current region figure image data to generate combined image data.

According to a third aspect of the invention, there is provided a medical image processing apparatus which processes X-ray transmission data collected by an X-ray rotational photographing mechanism, comprising:

a storage unit which stores a plurality of pieces of human anatomy figure image data collected by photographing a subject before the injection of a contrast media at a plurality of projection angles and a plurality of pieces of contrast image data collected by photographing the subject after the injection of the contrast media at the plurality of projection angles;

a subtraction unit which subtracts the contrast image data from the human anatomy figure image data, which are pieces of image data having the same projection angle concerning the photography, to generate contrast blood vessel figure data;

a first reconfiguration unit which executes reconfiguration processing based on the plurality of pieces of contrast blood vessel figure data generated by the subtraction unit to create contrast blood vessel figure three-dimensional image data;

a second reconfiguration unit which executes reconfiguration processing based on the plurality of pieces of human anatomy figure data to generate human anatomy figure three-dimensional image data;

a black-and-white reverse processing unit which executes black-and-white reverse processing with respect to the contrast blood vessel figure three-dimensional image data to generate non-blood-current figure three-dimensional image data; and a combination processing unit which combines the human anatomy figure three-dimensional image data with the non-blood-current figure three-dimensional image data to generate combined image data.

According to a fourth aspect of the invention, there is provided a medical image processing apparatus which processes data collected by an X-ray rotational photographing mechanism, comprising:

a storage unit which stores a plurality of pieces of human anatomy figure image data collected by photographing a subject before the injection of a contrast media at a plurality of projection angles and a plurality of pieces of contrast image data collected by photographing the subject after the injection of the contrast media at the plurality of projection angles;

a CT image storage unit which stores CT image data;

a subtraction unit which performs subtraction with respect to the contrast image data and the human anatomy figure image data which are pieces of image data having the same projection angle concerning the photography to generate contrast blood vessel figure data;

a reconfiguration unit which executes reconfiguration processing based on the plurality of pieces of contrast blood vessel figure data generated by the subtraction unit to generate contrast blood vessel figure three-dimensional image data, and executes reconfiguration processing based on the plurality of pieces of human anatomy figure data to generate human anatomy figure three-dimensional image data;

a reverse processing unit which executes black-and-white reverse processing with respect to the contrast blood vessel figure three-dimensional image data to generate a non-blood-current figure three-dimensional image data;

a displacement correction unit which detects displacement based on the human anatomy figure three-dimensional image data and the CT image data, and identifies and corrects three-dimensional displacement of the CT image data and the non-blood-current figure three-dimensional image data based on a result of the detection; and a combination processing unit which combines the non-blood-current figure three-dimensional image data and the displacement corrected CT image data to generate combined image data.

According to a fifth aspect of the invention, there is provided a medical image processing apparatus which processes X-ray transmission data collected based on photography by an X-ray rotational photographing mechanism at a plurality of projection angles, comprising:

a storage unit which stores first human anatomy figure image data including a non-contrast human anatomy figure and first contrast image data including a contrast blood vessel figure which are collected by the X-ray rotational photographing mechanism before a predetermined change in situation, and second human anatomy figure data including a non-contrast human anatomy and second contrast image data including a contrast blood vessel figure which are collected by the X-ray rotational photographing mechanism after the predetermined change in situation;

a first subtraction unit which subtracts the first contrast image data from the first human anatomy figure image data, which are pieces of image data having the same projection angle concerning the photography, to generate first contrast blood vessel figure data, and subtracts the second contrast image data from the second human anatomy figure image data, which are pieces of image data having the same projection angle concerning the photography, to generate second contrast blood vessel figure data;

a reconfiguration unit which generates first contrast blood vessel figure three-dimensional image data based on the first contrast blood vessel image data, generates second contrast blood vessel figure three-dimensional image data based on the second contrast blood vessel figure data, generates first human anatomy figure three-dimensional image data based on the first human anatomy figure image data, and generates second human anatomy figure three-dimensional image data based on the second human anatomy figure image data;

a displacement correction unit which identifies displacement of the subject based on the first human anatomy figure three-dimensional image data and the second human anatomy figure three-dimensional image data, and corrects displacement of the first contrast blood vessel three-dimensional image data or the second contrast blood vessel figure three-dimensional image data based on the identified displacement in such a manner a three-dimensional coordinate of the first contrast blood vessel figure three-dimensional image data becomes equal to that of the second contrast blood vessel figure three-dimensional image data;

a second subtraction unit which performs subtraction with respect to the first contrast blood vessel figure three-dimensional image data and the second contrast blood vessel figure three-dimensional image data which are corrected by the displacement correction unit to have the same three-dimensional coordinate, thereby generating blood current change figure three-dimensional image data; and a combination processing unit which combines the blood current change figure three-dimensional image data with the first human anatomy figure three-dimensional image data or the second human anatomy figure three-dimensional image data having the same three-dimensional coordinate as that of the blood current change figure three-dimensional image data to generate combined image data.

According to a sixth aspect of the invention, there is provided a medical image processing apparatus which processes X-ray transmission data collected based on photography by an X-ray rotational photographing mechanism at a plurality of projection angles, comprising:

a storage unit which stores first human anatomy figure/contrast blood vessel figure image data collected by the X-ray rotational photographing mechanism before a predetermined change in situation, and second human anatomy figure/contrast blood vessel figure image data and human anatomy figure image data collected by the X-ray rotational photographing mechanism after the predetermined change in situation;

a reconfiguration unit which generates first human anatomy/contrast blood vessel figure three-dimensional image data based on the first human anatomy/contrast blood vessel figure image data, and generates second human anatomy/contrast blood vessel figure three-dimensional image data based on the second human anatomy/contrast blood vessel figure image data;

a displacement correction unit which identifies displacement of a subject based on the first human anatomy/contrast blood vessel figure three-dimensional image data and the second human anatomy/contrast blood vessel figure three-dimensional image data, and corrects displacement of the first human anatomy/contrast blood vessel figure three-dimensional image data or the second human anatomy/contrast blood vessel figure three-dimensional image data based on the identified displacement;

a second subtraction unit which performs subtraction with respect to the first human anatomy/contrast blood vessel figure three-dimensional image data and the second human anatomy/contrast blood vessel figure three-dimensional image data which are corrected by the displacement correction unit to have the same three-dimensional coordinate, and thereby generates blood current change figure image data; and a combination processing unit which combines the blood current change figure image data with the first human anatomy/contrast blood vessel figure three-dimensional image data or the second human anatomy/contrast blood vessel figure three-dimensional image data having the same three-dimensional coordinate as that of the blood current change figure image data to generate combined image data.

According to a seventh aspect of the invention, there is provided a medical image processing apparatus which processes X-ray transmission data collected based on photography by an X-ray rotational photographing mechanism at a plurality of projection angles, comprising:

a storage unit which stores first human anatomy figure/contrast blood vessel figure image data collected by the X-ray rotational photographing mechanism before a predetermined change in situation, and a plurality of pieces of second human anatomy figure/contrast blood vessel figure image data and human anatomy figure image data collected by the X-ray rotational photographing mechanism after the predetermined change in situation;

a first subtraction unit which subtracts the second contrast image data from the second human anatomy figure image data, which are pieces of image data having the same projection angle concerning the photography, to generate second contrast blood vessel figure data;

a reconfiguration unit which generates first human anatomy/contrast blood vessel figure three-dimensional image data based on the first human anatomy/contrast blood vessel figure image data, and generates second human anatomy figure three-dimensional image data based on the second human anatomy figure image data;

a displacement correction unit which identifies displacement of a subject based on the first human anatomy/contrast blood vessel figure three-dimensional image data and the second human anatomy figure three-dimensional image data, and corrects displacement of the first human anatomy/contrast blood vessel figure three-dimensional image data based on the identified displacement;

a second subtraction unit which performs subtraction with respect to the first human anatomy/contrast blood vessel figure three-dimensional image data and the second human anatomy figure three-dimensional image data which are subjected to displacement correction by the displacement correction unit to have the same three-dimensional coordinate, and thereby generates first contrast blood vessel figure three-dimensional image data;

a third subtraction unit which performs subtraction with respect to the first contrast blood vessel figure three-dimensional image data and the second contrast blood vessel figure three-dimensional image data to generate blood current change figure image data; and combination processing unit which combines the blood current change figure image data with the second human anatomy figure three-dimensional image data to generate combined image data.

According to a eighth aspect of the invention, there is provided a medical image processing method for processing X-ray transmission data collected by an X-ray rotational photographing mechanism, comprising:

a first image generation step of executing reconfiguration processing based on the X-ray transmission data to generate contrast blood vessel figure three-dimensional image data including a contrast blood figure image;

a second image generation step of executing reconfiguration processing based on the X-ray transmission data to reconfigure human anatomy figure three-dimensional image data including a non-contrast human anatomy figure;

a reverse image processing step of executing black-and-white reverse processing with respect to the contrast blood vessel figure three-dimensional image data to generate reversed image data; and a combination processing step of combining the human anatomy figure three-dimensional image data with the reversed image data to generate combined image data.

According to a ninth aspect of the invention, there is provided a medical image processing method for processing X-ray transmission data collected by an X-ray rotational photographing mechanism, comprising:

a first image generation step of executing reconfiguration processing based on the X-ray transmission data to generate contrast blood vessel figure three-dimensional image data including a contrast blood vessel figure;

a second image generation step of executing reconfiguration processing based on the X-ray transmission data to generate human anatomy figure three-dimensional image data including a non-contrast human anatomy image;

an image processing step of generating low-blood current image data indicative of a low-blood current region based on the contrast blood vessel figure three-dimensional image data; and a combination processing step of combining the human anatomy figure three-dimensional image data with the low-blood current image data to generate combined image data.

According to a tenth aspect of the invention, there is provided a medical image processing method for processing X-ray transmission data collected by an X-ray rotational photographing mechanism, comprising:

a storage step of storing a plurality of pieces of human anatomy figure image data collected by photographing a subject before the injection of a contrast media at a plurality of projection angles and a plurality of pieces of contrast image data collected by photographing the subject after the injection of the contrast media at the plurality of projection angles;

a subtraction step of subtracting the contrast image data from the human anatomy figure image data, which are pieces of image data having the same projection angle concerning the photography, to generate contrast blood vessel figure data;

a first reconfiguration step of executing reconfiguration processing based on the plurality of pieces of contrast blood vessel figure data generated at the subtraction step to generate contrast blood vessel figure three-dimensional image data;

a second reconfiguration step of executing reconfiguration processing based on the plurality of pieces of human anatomy figure data to generate human anatomy figure three-dimensional image data;

a reverse processing step of executing black-and-white reverse processing with respect to the contrast blood vessel figure three-dimensional image data to generate non-blood-current figure three-dimensional image data; and a combination processing step of combining the human anatomy figure three-dimensional image data with the non-blood-current figure three-dimensional image data to generate combined image data.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing a structural example of a three-dimensional X-ray diagnostic apparatus according to a first embodiment of the present invention;

FIG. 2 is a view showing a flow of processing performed by a control unit in the first embodiment in light of processing contents;

FIG. 3A is a view showing a characteristic curve of "a voxel value–a value after LUT conversion" in black-and-white reverse processing of a DSA three-dimensional image data based on an LUT;

FIG. 3B is a view showing an example of a relationship between a pixel value and a reflection factor;

FIG. 4 is a view showing a flow of processing performed by a control unit in a first modification of the first embodiment in light of processing contents;

FIG. 6 is a view showing a flow of processing performed by a control unit in a second embodiment in light of processing contents;

DETAILED DESCRIPTION OF THE INVENTION

[First Embodiment]

Figure 5:
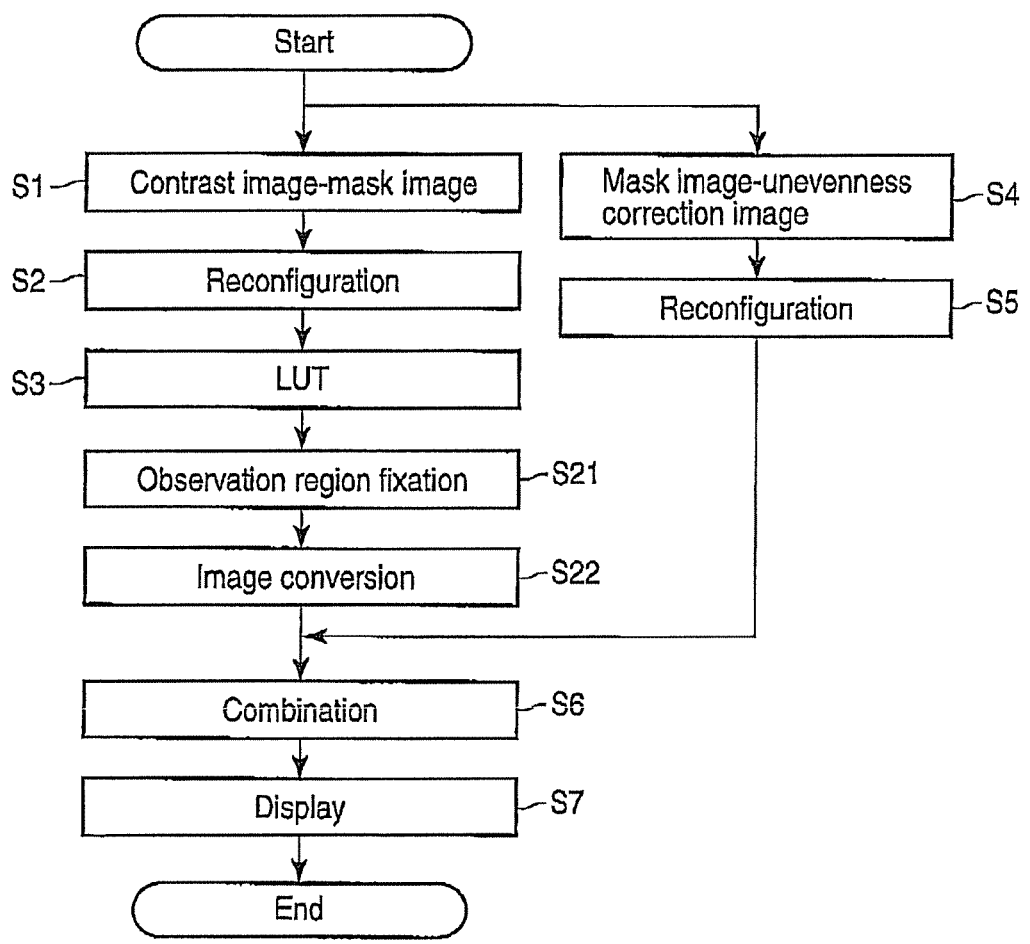
FIG. 5 is a view showing a flow of processing performed by a control unit in a second modification of the first embodiment in light of processing contents.

A medical image processing apparatus and a medical image processing method according to a first embodiment of the present invention will now be described hereinafter with reference to the drawings.

FIG. 1 is a view showing a structural example of a three-dimensional X-ray diagnostic apparatus to which a medical image processing apparatus according to this first embodiment is applied. As shown in FIG. 1, the three-dimensional X-ray diagnostic apparatus includes an X-ray photographing mechanism 10 and a medical image processing apparatus 1 according to this first embodiment.

The X-ray photographing mechanism 10 has an X-ray generation unit including an X-ray bulb 12, a detection system 14, a C-shaped arm 160 and a mechanism unit that moves the C-shaped arm 16. The detection system 14 is constituted of a flat panel detector (FPD) having a plurality of semiconductor detection elements arranged in a matrix form. The X-ray bulb 12 is mounted on the C-shaped arm 160 together with the detection system 14. A subject (not shown) laid on a top panel of a bed is arranged between the X-ray bulb 12 and the detection system 14. The C-shaped arm 160 is supported by a column support suspended from a ceiling. The C-shaped arm 160 can rotate on three axes A, B and C orthogonal to each other.

The X-ray generation unit includes the X-ray bulb 12 that irradiates the subject (not shown) with X-rays, a compensation filter (not shown) that reduces an absorption difference in X-rays, and an X-ray diaphragm (not shown) which sets an irradiation range of X-rays emitted from the X-ray bulb 12.

The compensation filter (not shown) is arranged between the X-ray bulb 12 and the subject and includes a filter and a filter driving mechanism which moves this filter. When this filter driving mechanism sets the compensation filter at a position meeting photography conditions, X-rays passing through the compensation filter are partially absorbed.

The X-ray diaphragm (not shown) is arranged between the X-ray bulb 12 and the subject and includes an upper blade, a lower blade and an X-ray diaphragm aperture driving mechanism which moves the upper blade and the lower blade. When this X-ray diaphragm aperture driving mechanism sets the upper blade and the lower blade at positions meeting the photography conditions, an irradiation range of X-rays is set.

The mechanism unit (not shown) includes an C-shaped arm swiveling/moving mechanism that swivels and slides the C-shaped arm 160, a top panel moving mechanism that moves the top panel in a longitudinal direction, a widthwise direction and a vertical direction or swivels the same in a horizontal state, a column support swiveling/moving mechanism that swivels and moves the column support that holds the C-shaped arm 160, and a C-shaped arm/top panel mechanism control unit that controls the C-shaped arm swiveling/moving mechanism, the top panel moving mechanism and the column support swiveling/moving mechanism.

The medical image processing apparatus 1 has a control unit 37, an A/D converter 21, a 3D image memory 23, a 2D image memory 24, a subtraction unit 31, an *affine* transform unit 36, a three-dimensional reconfiguration processing unit 33, a three-dimensional image processing unit 35, a D/A converter 38, a display unit 41 and a look-up table 45 (which will be referred to as an LUT hereinafter) 45.

The control unit 37 collectively controls each unit in the medical image processing apparatus 1.

The A/D converter 21 is connected with the X-ray photographing mechanism 10 to digitize projection data supplied from the X-ray photographing mechanism 10 as analog information.

The D/A converter 38 is connected with the display unit 41 to convert image data into analog data to be supplied to the display unit 41.

The 2D image memory 24 stores projection data that is supplied from the X-ray photographing mechanism 10 and digitized by the A/D converter 21.

The 3D image memory 23 stores image data reconfigured by later-described processing.

The subtraction unit 31 executes subtraction (DSA: digital subtraction angiography) of image data.

The filtering unit 32 executes filtering processing, e.g., high-frequency accentuation processing.

The three-dimensional reconfiguration processing unit 33 reconfigures three-dimensional image data from data of a plurality of images associated with a plurality of projecting directions.

The three-dimensional image processing unit 35 executes rendering processing such as surface rendering or combination processing.

The affine transform unit 36 executes enlargement processing or movement processing with respect to image data.

The LUT 45 executes gradation conversion with respect to image data.

Processing based on control performed by the control unit 37 in the medical image processing apparatus according to this first embodiment will now be described hereinafter. FIG. 2 is a view showing a flow of processing performed by the control unit 37 in light of processing contents.

First, the control unit 37 collects a plurality of pieces of image data associated with a plurality of projecting directions for two times in total, i.e., before injecting a contrast media into a blood vessel of a subject and after injecting the contrast media by the X-ray photographing mechanism 10. Further, the thus acquired image data is stored in the 2D image memory 24.

Here, the image data acquired before injection of the contrast media is called mask image data. The mask image data is image data including an image of a bone and an image of a soft tissue. A pixel value in each image reflects an intrinsic X-ray transmission factor of each of the bone and the soft tissue. On the other hand, the image data acquired after injection of the contrast media is called a contrast image. The contrast image data is image data including an image of a bone, an image of a soft tissue and an image of a blood vessel having the contrast media injected thereto. A pixel value in an image of a bone reflects an intrinsic X-ray transmission factor of the bone. A pixel value in an image of a soft tissue reflects an intrinsic X-ray transmission factor of the soft tissue. Furthermore, a pixel value in an image of a blood vessel having the contrast media injected thereto reflects an intrinsic X-ray transmission factor of the contrast media flowing through the blood vessel rather than an intrinsic X-ray transmission factor of the blood vessel. It is to be noted that the X-ray transmission factor of the contrast media is very lower than the X-ray transmission factor of the blood vessel.

In fact, photography is repeated for 200 times at intervals of, e.g., 1° to obtain 200 (200 frames) mask images while the C-shaped arm 160 rotates (A or B) at a high speed. The 200 mask images are associated with 200 projecting directions. 200 contrast images acquired after injection of the contrast media are associated with 200 projecting directions. The 200 contrast images are associated with the 200 mask images, respectively. A given mask image and a contrast image associated therewith have the same projecting direction.

After the mask image data and the contrast image data are generated based on the above-described processing, the control unit 37 executes subtraction with respect to projection data at angles with which the mask image data and the contrast image data are associated to generate DSA image data by using the subtraction unit 31 and supplies this DSA image data to the three-dimensional reconfiguration processing unit 33 (a step S1).

Specifically, at the step S1, the subtraction unit 31 subtracts the plurality of pieces of mask image data having different projecting directions from the plurality of pieces of contrast images having different projecting directions. In more detail, the contrast image data is subtracted from each mask image data having the same projecting direction, thereby generating the plurality of pieces of DSA image data. Each DSA image data basically includes an image of the blood vessel having the contrast media injected thereto alone.

Moreover, the control unit 37 performs three-dimensional reconfiguration processing with respect to the plurality of pieces of DSA image data to generate DSA three-dimensional image data by using the three-dimensional reconfiguration processing unit 33 (a step S2). The DSA three-dimensional image data includes a three-dimensional image of the blood vessel having the contrast media injected thereto alone.

Specifically, as a reconfiguration method, a filtered back projection method suggested by Feldkamp et al. is general. An appropriate convolution filter such as Shepp & Logan or Ramachandran is applied to the 200 DSA images. The 200 DSA images which have been through the convolution filter are subjected to back projection arithmetic processing to generate DSA three-dimensional image data.

Here, a reconfiguration region is defined as a cylinder which is inscribed with an X-ray bundle for all directions of the X-ray bulb 12. The inside of this cylinder is three-dimensionally discretized with a length d at the central portion of the reconfiguration region projected to a width of one detection element in the detection system 14 which is, e.g., a detector. Therefore, a reconfigured image of data at a discrete point must be obtained. However, although an example of a discrete interval is shown here, this may differ depending on each apparatus or each manufacturer, and hence using a discrete interval defined in accordance with each apparatus can basically suffice.

After the DSA three-dimensional image data is generated by the above-described processing, the control unit 37 transfers the DSA three-dimensional image data to the LUT 45, and the LUT 45 is utilized to execute black-and-white reverse processing with respect to the DSA three-dimensional image data (a step S3). In more detail, the black-and-white reverse processing is executed based on y=−ax. In this expression, x is a voxel value, y is a value obtained after the LUT conversion, and a is an arbitrary coefficient.

The DSA three-dimensional image data before the reverse processing based on the LUT 45 includes images of an artery, a vein and a capillary blood vessel. On the other hand, in the DSA three-dimensional image after the reverse processing based on the LUT 45, images of the artery and the vein can be ignored in display, and an image of the capillary blood vessel can be slightly seen in display. On the other hand, a part having no blood current is very brightly displayed. The DSA three-dimensional image data after the reverse processing based on the LUT 45 is called non-blood-current figure three-dimensional image data or capillary blood flow vessel figure three-dimensional image data.

Meanwhile, the control unit 37 performs subtraction with respect to the mask image data and air-calibration image data to generate human anatomy figure image data by using the subtraction unit 31, and supplies this human anatomy figure image data to the three-dimensional reconfiguration processing unit 33 (a step S4).

Here, the air-calibration image data is image data collected by photography in a state nothing except air is present between the X-ray bulb 12 and the detection system 14.

Subsequently, the control unit 37 executes the three-dimensional reconfiguration processing with respect to the plurality of pieces of human anatomy figure image data to generate human anatomy figure three-dimensional image data by using the three-dimensional reconfiguration processing unit 33 (a step S5). It is to be noted that the detail of the three-dimensional reconfiguration processing is as described above. The human anatomy figure three-dimensional image data includes an image of a human anatomy of a part associated with an image of the non-blood-current figure three-dimensional image data.

It is to be noted that incidental information of the non-blood-current figure three-dimensional image data and the human anatomy figure three-dimensional image data processed based on a map has a description that these pieces of data are image data as targets of image combination processing. The three-dimensional image processing unit 35 combines the pieces of image data having the incidental information indicating that these pieces of image data are image data as targets of the image combination processing to generate image data that can be displayed.

The control unit 37 uses the three-dimensional image processing unit 35 to combine the non-blood-current figure three-dimensional image data with the human anatomy figure three-dimensional image data and further executes volume rendering processing to create a volume rendering combined image (a step S6). Additionally, this volume rendering combined image is output to the display unit 41 via the D/A converter 38 and displayed in the display unit 41 (a step S7).

In more detail, the non-blood-current figure three-dimensional image data is determined as V1(x,y,z), the human anatomy figure three-dimensional image data is determined as V2(x,y,z), and an opacity curve O1($d$) for converting the non-blood-current figure three-dimensional image data into an optical parameter such as a reflection factor and an opacity curve O2(d) for likewise converting the human anatomy figure three-dimensional image data into an optical parameter are set.

Here, the opacity curve is defined as such a shape as depicted in, e.g., FIG. 3B. That is, adjusting a window width (WW) and a window level (WL) enables selecting tissue information to be displayed.

Further, different colors are set to reflected light from the non-blood-current figure three-dimensional image data and reflected light from the human anatomy (figure) three-dimensional image data. For example, yellow green is assigned to the reflected light from the non-blood-current figure three-dimensional image data, and white is assigned to the reflected light from the human anatomy figure three-dimensional image data. Furthermore, when a position and an intensity of a light source are determined, a volume rendering figure can be calculated in accordance with a light intensity distribution in the light source, and a traveling trajectory of light and a trajectory of the reflected light. Here, for convenience sake of the explanation, assuming that the traveling trajectory of light is parallel light having a fixed intensity 10, the following expressions can be achieved.

$$VL(u, v) = VL_w(u, v) + VL_{LG}(u, v) \quad (1)$$

$$VL_w(u, v) = \sum_{M=1}^{N} \{I_M \times O_2(V_2(x, y, z)) \times S(V_2(x, y, z))\} \quad (2)$$

$$VL_{LG}(u, v) = \sum_{M=1}^{N} \{I_M \times O_1(V_1(x, y, z)) \times S(V_1(x, y, z))\} \quad (3)$$

S(a) is a function utilized to calculate a concentration gradient in the three-dimensional image data. For example, if the same concentration is vertical to traveling of light, a gradient value is high. On the other hand, if the same concentration is gettering closer to a parallel state with respect to traveling of light, the gradient value gets closer to 0. Moreover, IM is calculated as follows.

$$I_M = I_{M-1} \times \{1 - O_1(V_1(x,y,z)) - O_2(V_2(x,y,z))\} \quad (4)$$

Repeatedly executing these calculations along the traveling trajectory of light (M in this example) enables creating a volume rendering image VL(u,v).

Here, Expression (1) can be calculated by using a vector considering three primary colors, i.e., RGB. Furthermore, in place of using Expression (1), VLW(u,v) and VLLG(u,v) may be displayed in different layers, and permeation rates of both the layers may be adjusted to carry out image combination.

Meanwhile, when displaying the volume rendering combined image as the 3D combined image data in the display unit 41, the control unit 37 changes display colors depending on a figure derived from the non-blood-current figure three-dimensional image data and a figure derived from the human anatomy figure three-dimensional image data, thereby comprehensibly displaying a positional relationship between the human anatomy and the non-blood-current image.

Moreover, display conditions (colors, optical parameters, WL/WW and others) for each three-dimensional image data can be individually changed. Additionally, each three-dimensional image data can be individually subjected to image processing such as cutting. Further, a display changeover switch may be provided so that each three-dimensional image data can be solely displayed when the display changeover switch is pressed.

It is to be noted that, when a user makes reference to the 3D combined image data displayed in the display unit 41 to manually identify a blood current observation region and sets pixel values in regions other than the observation region in the non-blood-current figure image to 0, non-blood-current information in a non-observed region (e.g., a bone part, an extracranial part, an air part and others) can be omitted.

It is to be noted that this embodiment can be modified in many ways. For example, the black-and-white reverse processing is performed with respect to the DSA three-dimensional image data by using the LUT in this embodiment, but the same result can be obtained when the black-and-white reverse processing is effected with respect to the DSA image data based on y=−ax before reconfiguration. Further, although the contrast image data is subtracted from each mask image data having the same projecting direction as the contrast image data, the same result can be obtained when the mask image data is subtracted from each contrast image data having the same projecting direction as the mask image data. In case of subsequently performing the black-and-white reverse processing with respect to the DSA three-dimensional image data, this processing may be executed based on a characteristic curve (a voxel value–a value after LUT conversion) depicted in FIG. 3A in place of y=−ax. In this case, assuming that there is no noise, a completed infarction region is zero, but it sometimes actually takes a negative value due to an influence of noise. Therefore, this characteristic curve is suitable for visualizing the completed infarction region.

According to this first embodiment, it is possible to provide the medical image processing apparatus and the medical image processing method that can rapidly detect a part where recirculation of a brain blood flow has an abnormality arising from clog of, e.g., a peripheral blood vessel owing to a treatment using the X-ray intervention.

It is to be noted that, in some cases, a part having no blood current shown in a non-blood-current image rarely (less) has blood currents from the beginning because of the human anatomy except for a case that there is not blood current which arises from clog of, e.g., a peripheral blood vessel owing to a treatment using the X-ray intervention. According to the medical image processing apparatus and the medical image processing method of this first embodiment, a non-blood-current part can be selectively observed based on the human anatomy in display of the volume rendering combined image as the 3D combined image data, thus discriminating the above-described two cases.

[First Modification]

A "first modification" of the medical image processing apparatus and the medical image processing method according to the first embodiment will now be described hereinafter. It is to be noted that differences from the medical image processing apparatus and the medical image processing method according to the first embodiment will be described to avoid tautological explanation. In this first modification, a CT image is utilized as an image showing a human anatomy. In this case, the CT image and a non-blood-current figure image must be positioned. This positioning is carried out at steps S11 and S12 described below.

FIG. 4 is a view showing a flow of processing performed by the control unit 37 in light of processing contents. Processing from a step S1 to a step S5 is the same as processing having the same step numbers described in the first embodiment.

After the processing at the step S5, in, e.g., a patient front direction and a patient side direction, CT image data is projected to create CT projected image data under the same geometric conditions as those for image data collection based on rotational photography. Further, displacement is detected based on this CT projected image data and image data collected in the same projecting direction in image data collected based on rotational photography (a step S11).

Likewise, displacement is detected based on image data collected in any other projecting direction and CT projected image data created by projecting CT image data under the same geometric conditions as those of the image data (the step S11). It is to be noted that, as the actually utilized projecting directions, the patient front direction and the patient side direction are suitable. Furthermore, three-dimensional displacement of the CT image data and non-blood-current figure image data is identified to be corrected based on the two pieces of displacement data (a step S12).

Moreover, the control unit 37 uses the three-dimensional image processing unit 35 to combine the CT image data with the non-blood-current figure three-dimensional image data processed in a map (a step S13). Additionally, combined image data generated by this combination processing is displayed in the display unit 41 (a step S14). The detail of this combination processing and the display processing is as described above in the first embodiment, thereby omitting an explanation thereof.

As described above, according to this first modification, it is possible to provide the medical image processing apparatus and the medical image processing method that can demonstrate the same effects as those of the medical image processing apparatus and the medical image processing method according to the first embodiment and can facilitate display of a relationship between a brain structure and a blood current amount in more detail.

It is to be noted that displacement may be of course three-dimensionally identified based on an image reconfigured based on image data collected by rotational photography before the injection of the contrast media and a CT image and displacement of the CT image may be corrected based on the identified displacement.

[Second Modification]

A "second modification" of the medical image processing apparatus and the medical image processing method according to the first embodiment will now be described hereinafter. It is to be noted that differences from the medical image processing apparatus and the medical image processing method according to the first embodiment will be described to avoid tautological explanation. Although an observation region is identified based on a manual operation in the first embodiment, an observation region is automatically identified to some extent in this second modification.

FIG. 5 is a view showing a flow of processing performed by the control unit 37 in light of processing contents. Processing from a step S1 to a step S7 is the same as the processing having the same step numbers described in the first embodiment.

In this second modification, human anatomy figure three-dimensional image data is reconfigured based on a rotational photography image before the injection of the contrast media, a pixel value region of a bone is identified from this human anatomy figure three-dimensional image data, and a region corresponding to the inside of the identified pixel value region of the bone is identified as a cranial region as an observation region (a step S21). Furthermore, non-blood-current figure information of non-blood-current figure three-dimensional image data corresponding to a part other than the thus identified cranial region is deleted. It is to be noted that a CT image may be of course used as a human anatomy figure image.

Subsequently, at a step S22, processing for attenuating a pixel value is performed with respect to a part that essentially has almost no blood current in the cranial region. Specifically, the following processing is carried out (the step S22).

IMAGE PROCESSING EXAMPLE 1

The identified cranial region is compared with a standard cranial model, and the standard cranial model is subjected to warping so that it can match with the identified cranial region. Moreover, a brain structure of this warped cranial model is stored in a predetermined memory, and processing for attenuating a pixel value in non-blood-current figure three-dimensional image data is performed with respect to a part that essentially has almost no blood current based on the brain structure of the warped cranial model (the step S22).

IMAGE PROCESSING EXAMPLE 2

Human anatomy figure three-dimensional image data is reconfigured based on image data collected by rotational photography before the injection of the contrast media, and a pixel value at a soft tissue level is identified on this human anatomy figure three-dimensional image data. Additionally, the processing for attenuating a pixel value of a corresponding part in non-blood-current figure three-dimensional image data as the pixel value deviates from the identified pixel value is executed (the step S22).

IMAGE PROCESSING EXAMPLE 3

A brain tissue part is discriminated from any other part based on a CT image, and the processing for attenuating a pixel value in non-blood-current figure three-dimensional image data other than the brain tissue part is carried out (the step S22).

IMAGE PROCESSING EXAMPLE 4

A blood current part and any other part are extracted in a subtraction image of a projected image by threshold value processing, and each pixel of non-blood-current figure three-dimensional image data is projected in the patient front direction or the patient side direction based on the extracted parts. If a projection point is a part other than the blood current part, the processing for attenuating a pixel value in this region is performed (the step S22).

IMAGE PROCESSING EXAMPLE 5

A blood current part and any other part are extracted in a subtraction image of a projected image by threshold value processing. Each pixel of a non-blood-current image is projected in all directions based on the extracted information, and a projection angle range where a projection point corresponds to a part other than the blood current part is identified. The processing for attenuating a pixel value is performed in accordance with an angle of this range (the step S22).

As described above, according to this second modification, it is possible to provide the medical image processing apparatus and the medical image processing method that can demonstrate the same effects as the medical image processing apparatus and the medical image processing method according to the first embodiment and can automatically perform intensified display of a desired observation region when displaying 3D combined image data.

[Second Embodiment]

A medical image processing apparatus and a medical image processing method according to a second embodiment of the present invention will now be described hereinafter. It is to be noted that differences from the medical image processing apparatus and the medical image processing method according to the first embodiment will be described to avoid tautological explanation.

In the first embodiment, the control unit 37 collects a plurality of pieces of image data associated with a plurality of projecting directions for two times in total, i.e., before injecting a contrast media into a blood vessel of a subject and after injecting the contrast media by using the X-ray photographing mechanism 10.

On the other hand, in this second embodiment, image data collection is executed before and after injecting the contrast media before and after a "treatment such as a predetermined procedure or injection of a medication", e.g., dissolving a blood clot. That is, in this second embodiment, the image data collection is executed for four times in total. It is to be noted that collection of air-calibration image data is not counted in the number of times of photography since a picture of a subject is not taken as described above.

Specifically, the image data collection is performed for four times in total under the following conditions.

(Collection 1) Before a treatment such as a predetermined procedure or injection of a medication and before injection of the contrast media (Collection 2) Before a treatment such as a predetermined procedure or injection of a medication and after injection of the contrast media (Collection 3) After a treatment such as a predetermined procedure or injection of a medication and before injection of the contrast media (Collection 4) After a treatment such as a predetermined procedure or injection of a medication and after injection of the contrast media In this second embodiment,
mask image data collected in (Collection 1) is called first mask image data;
contrast image data collected in (Collection 2) is called first contrast image data;
mask image data collected in (Collection 3) is called second mask image data; and
contrast image data collected in (Collection 4) is called second contrast image data.

FIG. 6 is a view showing a flow of processing performed by a control unit 37 in light of processing contents.

First, after mask image data and contrast image data are generated based on the processing described in the first embodiment, the control unit 37 performs subtraction with respect to projection data at angles associated with first mask image data and first contrast image data to generate first DSA image data by using a subtraction unit 31, and supplies this first DSA image data to a three-dimensional reconfiguration processing unit 33 (a step S31).

Subsequently, the control unit 37 performs three-dimensional reconfiguration processing with respect to the plurality of pieces of first DSA image data to generate first DSA three-dimensional image data by using the three-dimensional reconfiguration processing unit 33 (a step S32). This first DSA three-dimensional image data includes a three-dimensional structure alone of a blood vessel having the contrast media injected thereto.

Further, the control unit 37 carries out subtraction with respect to projection data at angles associated with the first mask image data and air-calibration image data to generate first human anatomy figure image data by using the subtraction unit 31, and supplies this first human anatomy figure image data to the three-dimensional reconfiguration processing unit 33 (a step S33).

Furthermore, the control unit 37 executes three-dimensional reconfiguration processing with respect to the plurality of pieces of human anatomy figure image data to generate first human anatomy figure three-dimensional image data by using the three-dimensional reconfiguration processing unit 33 (a step S34).

Here, a user gives a subject a treatment such as a predetermined procedure or injection of a medication.

Moreover, after second mask image data and second contrast image data are generated based on the processing described in the first embodiment, the control unit 37 performs subtraction with respect to projection data at angles associated with the second mask image data and the second contrast image data to generate second DSA image data by using the subtraction unit 31, and supplies this second DSA image data to the three-dimensional reconfiguration processing unit 33 (a step S35).

Subsequently, the control unit 37 uses the three-dimensional reconfiguration processing unit 33 to perform three-dimensional reconfiguration processing with respect to the plurality of pieces of second DSA image data, thereby generating second DSA three-dimensional image data (a step S36). The second DSA three-dimensional image data includes a three-dimensional structure image alone of the blood vessel having the contrast media injected thereto.

Further, the control unit 37 performs subtraction with respect to projection data at angles associated with the second mask image data and the air-calibration image data to generate second human anatomy figure image data by using the subtraction unit 31, and supplies this second human anatomy figure image data to the three-dimensional reconfiguration processing unit 33 (a step S37).

Furthermore, the control unit 37 carries out three-dimensional reconfiguration processing with respect to the plurality of pieces of second human anatomy figure image data generated at the step S37 by using the three-dimensional reconfiguration processing unit 33, thereby generating second human anatomy figure three-dimensional image data (a step S38).

Here, the control unit 37 compares the first human anatomy figure three-dimensional image data with the second human anatomy figure three-dimensional image data to identify displacement of the subject (a step S39). Then, displacement of the first DSA three-dimensional image data is corrected based on the displacement identified at the step S39 (a step S40).

Thereafter, the control unit 37 performs subtraction with respect to projection data at angles associated with the first DSA three-dimensional image data and the second DSA three-dimensional image data to generate blood current change figure three-dimensional image data by using the subtraction unit 31 (a step S41).

According to this blood current change figure three-dimensional image data, a difference in blood current before and after performing, e.g., a predetermined procedure or injection of a medication is shown as a figure. In other words, according to the blood current change figure three-dimensional image data, how a blood current has been improved by a predetermined procedure or injection of a medication is shown as a figure.

The control unit 37 uses the three-dimensional image processing unit 35 to combine the blood current change figure three-dimensional image data with the human anatomy figure three-dimensional image data and carry out volume rendering processing to create a volume rendering combined image. Moreover, this volume rendering combined image is output to the display unit 41 via the D/A converter 38 to be displayed in the display unit 41.

As described above, according to this second embodiment, the same effects as the medical image processing apparatus and the medical image processing method according to the first embodiment can be demonstrated, and a difference in blood current before and after performing a predetermined procedure such as dissolving a blood clot or injection of a medication can be displayed as a figure. Therefore, the medical image processing apparatus and the medical image processing method that enable visually confirming how a blood current has been improved by a predetermined treatment of injection of a medication can be provided.

[Third Embodiment]

A medical image processing apparatus and a medical image processing method according to a third embodiment will now be described hereinafter. It is to be noted that differences from the medical image processing apparatus and the medical image processing method according to the second embodiment will be described to avoid tautological explanation. In the second embodiment, image data collection is performed once before and after injecting a contrast media before and after "a treatment such as a predetermined procedure or injection of a medication", e.g., dissolving a blood clot. That is, in this second embodiment, image data collection is carried out for four times in total.

In this third embodiment, the collection of the first mask image data and the second mask image data in the second embodiment is not effected. Therefore, the number of times of collecting the image data is smaller than that in the second embodiment by two. It is to be noted that the collection of air-calibration image data is not counted in the number of times of photography since a picture of a subject is not taken as described above.

Specifically, in the third embodiment, the image data collection is performed twice in total under the following conditions.

(Collection 1) Before a treatment such as a predetermined procedure or injection of a medication and after injection of a contrast media; the collection of first contrast image data (Collection 2) After a treatment such as a predetermined procedure or injection of a medication and after injection of a contrast media; the collection of second contrast image data.

Figure 7:
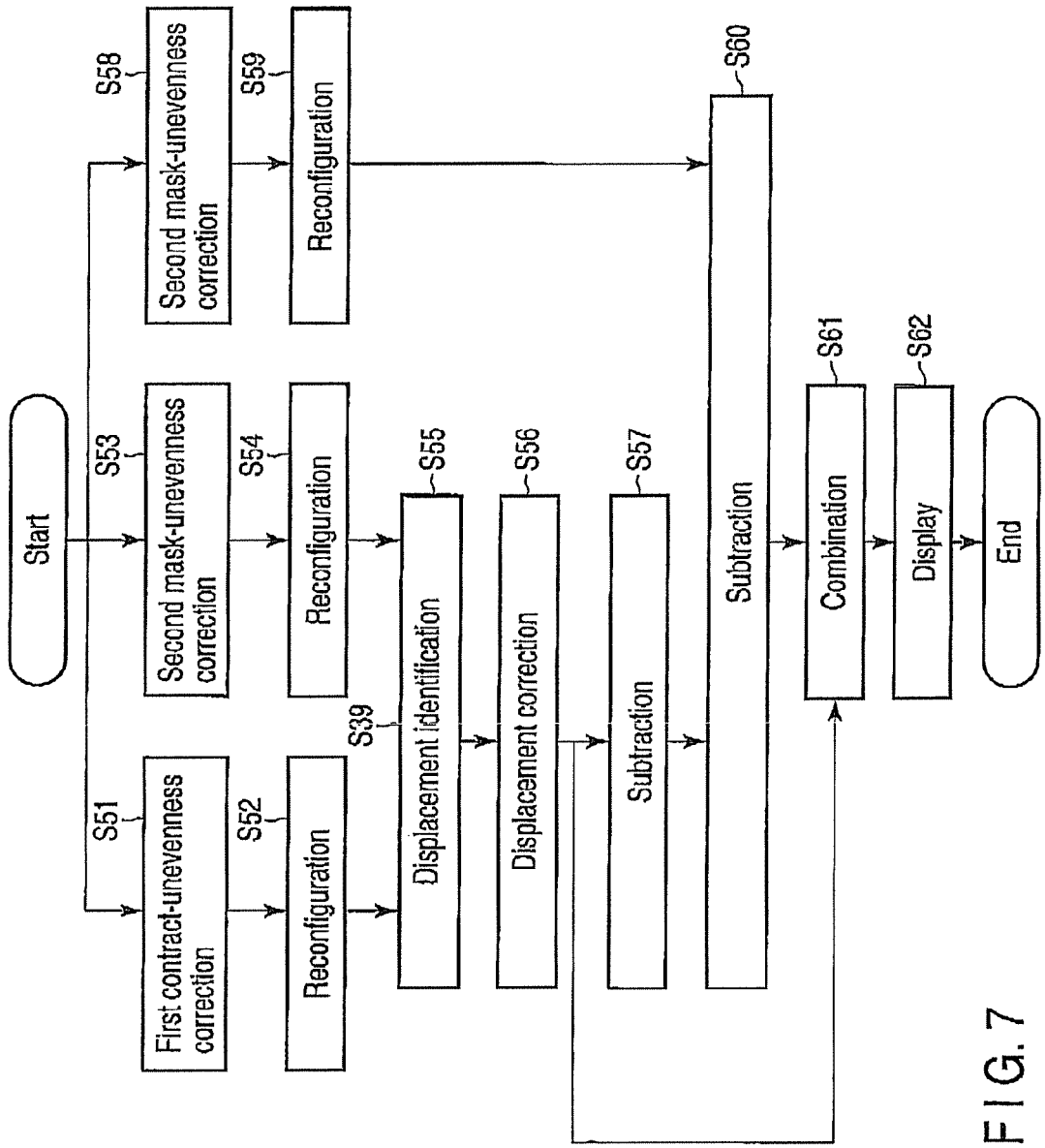
FIG. 7 is a view showing a flow of processing performed by a control unit in a third embodiment in light of processing contents.

FIG. 7 is a view showing a flow of processing performed by a control unit 37 in light of processing contents.

First, the control unit 37 performs subtraction with respect to the first contrast image data and air-calibration image data to generate a plurality of pieces of first human anatomy/contrast blood vessel figure data by using a subtraction unit 31, and supplies these pieces of first human anatomy/contrast blood vessel figure data to a three-dimensional reconfiguration processing unit 33 (a step S51).

Subsequently, the control unit 37 uses the three-dimensional reconfiguration processing unit 33 to perform three-dimensional reconfiguration processing with respect to the plurality of pieces of first human anatomy/contrast blood vessel figure data, thereby generating first human anatomy/contrast blood vessel figure three-dimensional image data (a step S52).

Furthermore, the control unit 37 effects subtraction with respect to projection data at angles associated with second mask image data and the air-calibration image data to generate first human anatomy figure image data by using the subtraction unit 31, and supplies this first human anatomy figure image data to the three-dimensional reconfiguration processing unit 33 (a step S53).

Moreover, the control unit 37 uses the three-dimensional reconfiguration processing unit 33 to effect three-dimensional reconfiguration processing with respect to the plurality of pieces of human anatomy figure image data, thereby generating first human anatomy figure three-dimensional image data (a step S54).

Here, the control unit 37 compares the first human anatomy/contrast blood vessel figure three-dimensional image data with the first human anatomy figure three-dimensional image data to identify displacement of the subject (a step S55). Subsequently, displacement of the first human anatomy/contrast blood vessel three-dimensional image data is corrected based on the displacement detected at the step S55 (a step S56).

Then, the control unit 37 carries out subtraction with respect to projection data at angles associated with the first human anatomy/contrast blood vessel figure three-dimensional image data by using the subtraction unit 31, thereby generating first contrast blood vessel figure three-dimensional image data (a step S57).

The control unit 37 performs subtraction with respect to projection data at angles associated with the second mask image data and second contrast image data to generate second contrast blood vessel figure image data by using the subtraction unit 31, and supplies this second contrast blood vessel figure image data to the three-dimensional reconfiguration processing unit 33 (a step S58).

Subsequently, the control unit 37 uses the three-dimensional reconfiguration processing unit 33 to effect three-dimensional reconfiguration processing with respect to the plurality of pieces of second contrast blood vessel figure image data, thereby generating second blood vessel figure three-dimensional image data (a step S59).

Here, the first contrast blood vessel figure three-dimensional image data is three-dimensional image data including a contrast blood vessel figure before a treatment such as a predetermined procedure or injection of a medication alone. On the other hand, the second contrast blood vessel figure three-dimensional image data is three-dimensional image data including a contrast blood vessel image after a treatment such as a predetermined procedure or injection of a medication alone.

Moreover, the control unit 37 effects subtraction with respect to the first contrast blood vessel figure image data and the second contrast blood vessel figure image data to generate a plurality of pieces of blood current change figure three-dimensional image data by using a three-dimensional image processing unit 35 (a step S60). Additionally, the blood current change figure three-dimensional image data is combined with the first human anatomy figure three-dimensional image data (a step S61). Further, this combined image is output to a display unit 41 via a D/A converter 38 to be displayed in the display unit 41 (a step S62).

As described above, according to this third embodiment, it is possible to provide the medical image processing apparatus and the medical image processing method that can demonstrate the same effects as the medical image processing apparatus and the medical image processing method according to the second embodiment and can reduce an X-ray exposure amount in the subject.

[Fourth Embodiment]

A medical image processing apparatus and a medical image processing method according to a fourth embodiment of the present invention will now be described hereinafter. It is to be noted that differences from the medical image processing apparatus and the medical image processing method according to the second embodiment will be described to avoid tautological explanation. In the second embodiment, image data collection is carried out for four times. In this fourth embodiment, since the collection of first mask image data and second mask image data is not performed, the number of times of collecting image data is smaller than that in the second embodiment by two. It is to be noted that the collection of air-calibration image data is not counted in the number of times of photography since a picture of a subject is not taken as described above.

Specifically, in this fourth embodiment, image data collection is carried out twice in total under the following conditions.

(Collection 1) Before a treatment such as a predetermined procedure or injection of a medication and after injection of a contrast media; the collection of first contrast image data.

(Collection 2) After a treatment such as a predetermined procedure or injection of a medication and after injection of a contrast media; the collection of second contrast image data.

Figure 8:
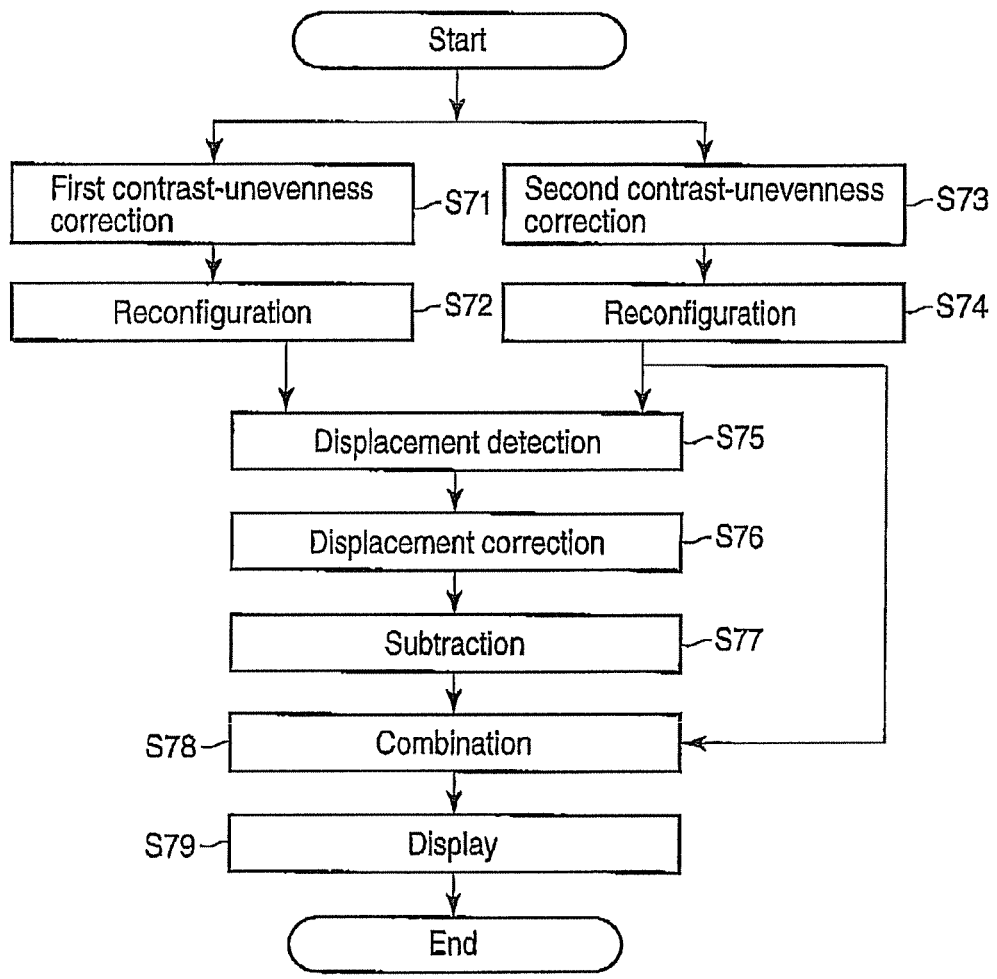
FIG. 8 is a view showing a flow of processing performed by a control unit in a fourth embodiment in light of processing contents.

FIG. 8 is a view showing a flow of processing performed by a control unit 37 in light of processing contents.

First, after a plurality of pieces of first contrast image data and air-calibration image data are generated, the control unit 37 performs subtraction with respect to the first contrast image data and the air-calibration image data to generate a plurality of pieces of first human anatomy/contrast blood vessel figure data by using a subtraction unit 31, and supplies these pieces of first human anatomy/contrast blood vessel figure data to a three-dimensional reconfiguration processing unit 33 (a step S71).

Further, the control unit 37 uses the three-dimensional reconfiguration processing unit 33 to effect three-dimensional reconfiguration processing with respect to the plurality of pieces of first human anatomy/contrast blood vessel figure data, thereby generating first human anatomy/contrast blood vessel figure three-dimensional image data (a step S72). This human anatomy/contrast blood vessel figure three-dimensional image data includes a human anatomy figure and a blood vessel contrast figure at a point in time before performing a treatment such as a predetermined procedure or injection of a medication.

Here, a treatment such as a predetermined procedure or injection of a mediation is carried out with respect to the subject.

Furthermore, after a plurality of pieces of second contrast image data are generated, the control unit 37 carries out subtraction of the second contrast image data and the air-calibration image data to generate a plurality of pieces of second human anatomy/contrast blood vessel figure data by using a subtraction unit 31, and supplies these pieces of second human anatomy/contrast blood vessel figure data to the three-dimensional reconfiguration processing unit 33 (a step S73).

Subsequently, the control unit 37 performs three-dimensional reconfiguration processing with respect to the plurality of pieces of second human anatomy/contrast blood vessel figure data by using the three-dimensional reconfiguration processing unit 33, thereby generating second human anatomy/contrast blood vessel figure three-dimensional image data (a step S74). The second human anatomy/contrast blood vessel figure three-dimensional image data includes a human anatomy figure and a blood vessel contrast figure at a point in time after effecting the treatment, e.g., the predetermined procedure or injection of a medication.

Here, the control unit 37 compares the first human anatomy/contrast blood vessel figure three-dimensional image data and with the second human anatomy/contrast blood vessel figure three-dimensional image data to identify displacement of the subject (a step S75). Here, information of a pixel value corresponding to a bone alone is extracted from the first human anatomy/contrast blood vessel figure three-dimensional image data and the second human anatomy/contrast blood vessel figure three-dimensional image data, and displacement is identified by using the extracted bone information alone, thereby accurately identifying the displacement. Subsequently, displacement of the first human anatomy/contrast blood vessel figure three-dimensional image data is corrected based on the displacement identified at the step S75 (a step S76).

Thereafter, the control unit 37 performs subtraction with respect to projection data at angles associated with a first human anatomy/contrast blood vessel figure volume and the second human anatomy/contrast blood vessel figure three-dimensional image data by using the subtraction unit 31, thereby generating blood current change figure three-dimensional image data (a step S77).

The control unit 37 uses a three-dimensional image processing unit 35 to combine the blood current change figure three-dimensional image data with the human anatomy/contrast blood vessel figure three-dimensional image data and performs volume rendering processing to create a volume rendering combined image. Moreover, this volume rendering combined image is output to a display unit 41 via a D/A converter 38 to be displayed in the display unit 41.

As described above, according to this fourth embodiment, it is possible to provide the medical image processing apparatus and the medical image processing method that can demonstrate the same effects as those of the medical image processing apparatus and the medical image processing method according to the third embodiment and can further reduce an X-ray exposure amount in the subject.

Although the present invention has been described above based on the first embodiment to the fourth embodiment, the present invention is not restricted to the foregoing embodiments, and it can be of course modified and applied in many ways within the scope of the present invention.

Additionally, the foregoing embodiments include inventions on various stages, and various inventions can be obtained by appropriately combining a plurality of disclosed structural requirements. For example, when the problem described in the section "problems to be solved by the invention" can be solved and the effects described in the section "effect of the invention" can be obtained even though several structural requirements are deleted from all structural requirements disclosed in the embodiments, a configuration from which these structural requirements have been deleted can be acquired as the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical image processing apparatus which processes X-ray transmission data collected by an X-ray rotational photographing mechanism, comprising:
  a memory which stores a plurality of pieces of human anatomy figure image data collected by photographing a subject before the injection of a contrast media at a plurality of projection angles and a plurality of pieces of contrast image data collected by photographing the subject after the injection of the contrast media at the plurality of projection angles;
  a subtraction unit which subtracts the contrast image data from the human anatomy figure image data, which are pieces of image data having the same projection angle concerning the photography, to generate contrast blood vessel figure data;
  a first reconfiguration unit implemented by circuitry which executes reconfiguration processing based on the plurality of pieces of contrast blood vessel figure data generated by the subtraction unit to create contrast blood vessel figure three-dimensional image data;
  a second reconfiguration unit implemented by circuitry which executes reconfiguration processing based on the plurality of pieces of human anatomy figure data to generate human anatomy figure three-dimensional image data;
  a black-and-white reverse processing unit implemented by circuitry which executes black-and-white reverse processing with respect to the contrast blood vessel figure three-dimensional image data to generate capillary blood flow vessel figure three-dimensional image data for enhancing a display of blood flow in capillary blood vessels over arteries and veins; and
  a combination processing unit implemented by circuitry which combines the human anatomy figure three-dimensional image data with the capillary blood flow vessel figure three-dimensional image data to generate combined image data.

2. The apparatus according to claim 1, including a non-region-of-interest deletion unit implemented by circuitry which identifies an observation target region in the human anatomy figure three-dimensional image data and deletes regions other than a region corresponding to the observation target region in the capillary blood flow vessel figure three-dimensional image data.

3. The apparatus according to claim 2, wherein the non-region-of-interest deletion unit implemented by circuitry identifies the observation target region based on pixel values in the human anatomy figure three-dimensional image data and attenuates pixel values of regions other than a region corresponding to the observation target region in the capillary blood flow vessel figure three-dimensional image data.

4. The apparatus according to claim 3, wherein a pixel value of the observation target region is a pixel value indicative of a soft tissue level.

5. The apparatus according to claim 2, wherein the non-region-of-interest deletion unit includes a non-region-of-interest deletion unit which identifies an observation target region based on a CT value in a CT image and deletes regions other than a region corresponding to the observation target region in the capillary blood flow vessel figure three-dimensional image data.

6. A medical image processing method for processing X-ray transmission data collected by an X-ray rotational photographing mechanism, comprising:
  storing a plurality of pieces of human anatomy figure image data collected by photographing a subject before the injection of a contrast media at a plurality of projection angles and a plurality of pieces of contrast image data collected by photographing the subject after the injection of the contrast media at the plurality of projection angles;
  subtracting the contrast image data from the human anatomy figure image data, which are pieces of image data having the same projection angle concerning the photography, to generate contrast blood vessel figure data;
  executing reconfiguration processing based on the plurality of pieces of contrast blood vessel figure data generated at the subtraction step to generate contrast blood vessel figure three-dimensional image data;
  executing reconfiguration processing based on the plurality of pieces of human anatomy figure data to generate human anatomy figure three-dimensional image data;
  executing black-and-white reverse processing with respect to the contrast blood vessel figure three-dimensional image data to generate capillary blood flow vessel figure three-dimensional image data for enhancing a display of blood flow in capillary blood vessels over arteries and veins; and
  combining the human anatomy figure three-dimensional image data with the capillary blood flow vessel figure three-dimensional image data to generate combined image data.

* * * * *